United States Patent

Marinenko

[11] 3,966,413
[45] June 29, 1976

[54] ELECTROCHEMICAL CHLORINE FLUX MONITOR

[75] Inventor: George Marinenko, Clarksburg, Md.

[73] Assignee: The United States of America as represented by the Secretary of Commerce, Washington, D.C.

[22] Filed: Sept. 5, 1975

[21] Appl. No.: 610,711

[52] U.S. Cl. .......................... 23/253 R; 23/230 R; 204/195 R; 324/30 R
[51] Int. Cl.² ................. G01N 27/46; G01N 27/52
[58] Field of Search ..................... 204/1 b, 195 R; 23/230 R, 253 R

[56] References Cited
UNITED STATES PATENTS

| | | | |
|---|---|---|---|
| 2,585,811 | 2/1952 | Marks | 204/1 B |
| 3,902,982 | 9/1975 | Nakagawa | 204/195 R |

Primary Examiner—G. L. Kaplan
Attorney, Agent, or Firm—David Robbins; Eugene J. Pawlikowski; Alvin Englert

[57] ABSTRACT

This apparatus for monitoring the chlorine concentration of water has a unique internal calibration capability and a high sensitivity. A water sample is mixed with a solution of potassium iodide and the reaction produces a mole of iodine for every mole of chlorine present in the water. The mixture is passed through a detection and calibration assembly wherein the iodine is detected amperometrically by a detection cell. Calibrant (known) iodine fluxes, equivalent in effect to the unknown chlorine-produced iodine fluxes, are supplied to the detection cell during calibration runs by means of an upstream calibration cell which electrolyzes the iodide (preferably added to distilled water) to iodine at flux rates given simply by the electrolyzing currents divided by Faraday's constant. An electronics package having gain and offset controls and a concentration display is provided.

6 Claims, 6 Drawing Figures

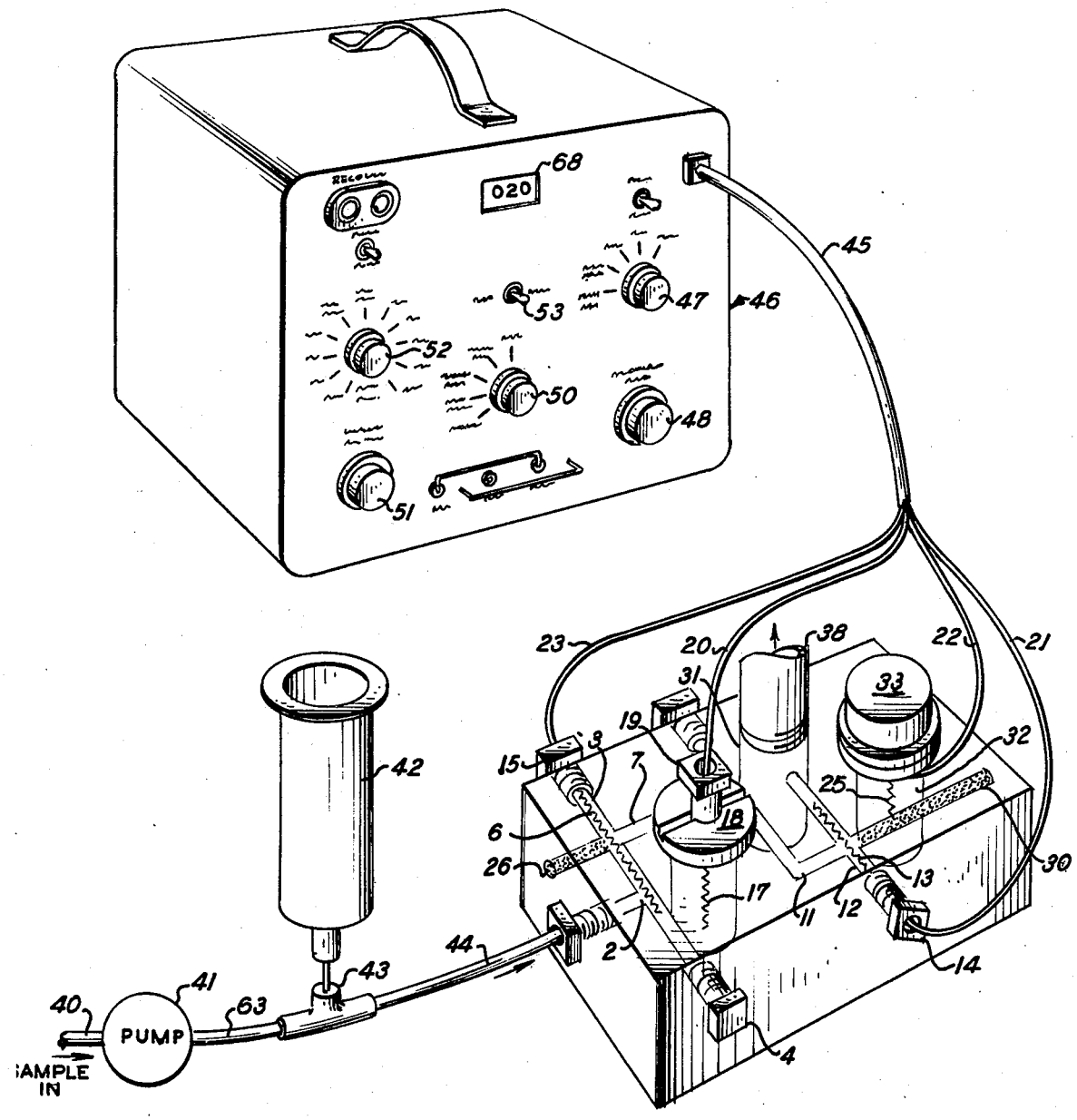

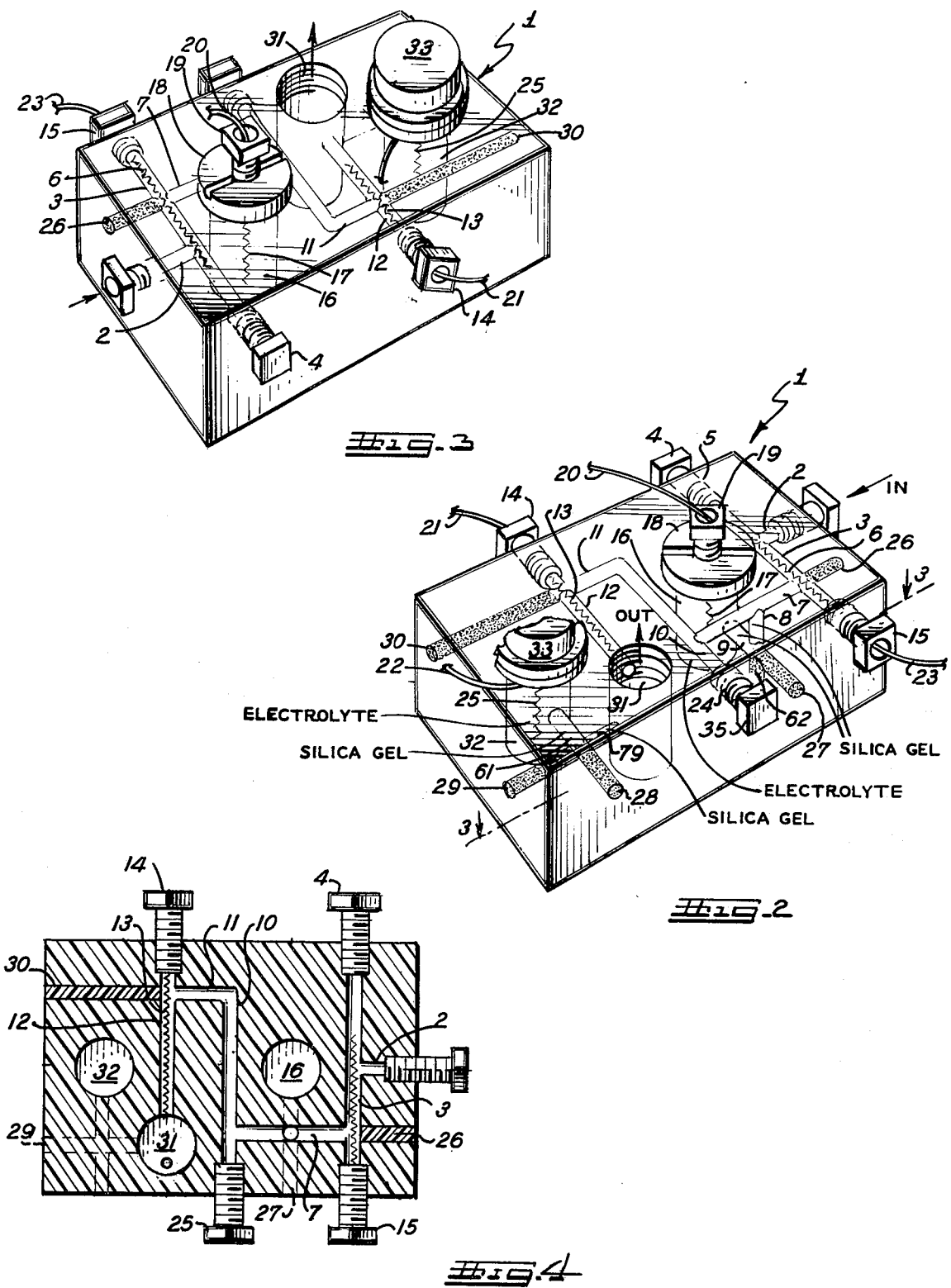

ELECTROCHEMICAL CHLORINE FLUX MONITOR

The present invention relates to an apparatus for monitoring the chlorine concentration of water. The apparatus of the invention has a built-in calibration feature not found in prior art chlorine monitors as well as a high sensitivity.

Growing concern has recently been focused on the environmental effects of chlorine and chlorine derivatives in aqueous ecosystems. Sewage treatment plants and power plants are the principal contributors of these contaminants to natural water systems. In sewage treatment plants chlorine is used to disinfect the sewage and decrease biochemical oxygen demand while in the power plants it is generally used to control fouling in heat exchangers. The sewage treatment plants contribute larger amounts of chlorine than the power plants and have caused massive fish kills in some areas.

To investigate the concentration of chlorine, a self-contained instrument which may be used in the natural waters, for instance when working off of a ship, is necessary. The instrument should provide a means for calibrating itself other than by using a standard solution of a reducing agent, such as As (III). This is because preparation of standard solutions in the field is not convenient and prolonged storage of the solutions results in slow oxidation of the reducing agent by air oxygen. Additionally, the instrument should provide a sensitivity down to parts per billion of chlorine as environmental investigations require information down to this order of magnitude.

It is thus an object of the invention to provide an apparatus for measuring the concentration of chlorine in water which has a built-in, self-contained calibration means.

It is a further object of the invention to provide an apparatus for measuring the concentration of chlorine in water which has a high sensitivity.

The above objects are accomplished by mixing water drawn from a sample to be monitored with a potassium iodide solution. The reaction yields a mole of iodine for each mole of chlorine present in the water. The iodine concentration is then monitored amperometrically by passing the potassium iodide/water solution between the electrodes of an iodine detecting cell means. The current generated by the cell is proportional to the amount of iodine present and a measured value of the current converted to concentration of chlorine is displayed.

The instrument is calibrated by providing an electrolysis cell means for coulometrically generating iodine from potassium iodide which cell is disposed upstream of the detecting cell means. According to Faraday's Law, when a current is applied to the electrolysis cell, an amount of iodine proportional to the current is generated. Since the amount of iodine added by the electrolysis to that released by the chemical reaction between the potassium iodide and the chlorine is known (if distilled water is used for calibrating the latter iodine value is approximately zero), the apparatus may be calibrated.

The invention will be better understood by referring to the drawings which show an illustrative embodiment thereof, and in which:

FIG. 1 is an overall showing of the chlorine monitoring apparatus of the invention.

FIGS. 2 and 3 are perspective views taken from opposite sides of the detecting and calibrating assembly of the apparatus.

FIG. 4 is a sectional view of the assembly of FIG. 2 taken at plane 3—3.

Figure 5:
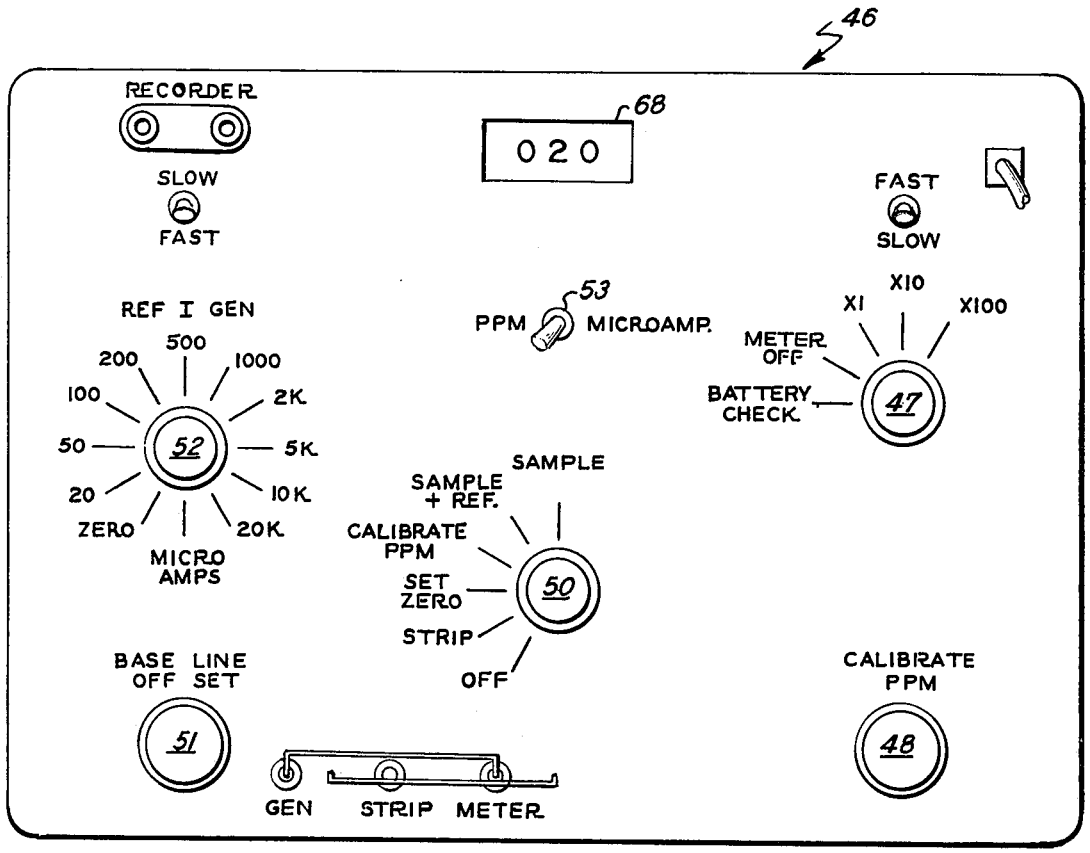
FIG. 5 is a drawing illustrating typical controls which may be found on the face-plate of the electronics package of the apparatus.

Referring to FIGS. 2, 3, and 4, the detecting and calibrating assembly 1 of the invention is shown in detail. In the illustrative embodiment fluid is transported past both the calibrating cell means and the detecting cell means by passageways drilled in a plastic (for example, polymethacrylate) block. The detecting cell is comprised of working electrode 13 disposed in passageway 12 by threaded plastic mounting means 14, and reference electrode 25 disposed in vertical passageway 32 which is filled with an electrolyte. In FIG. 2 electrode cap 33 is disposed over the electrode. While any appropriate combination of materials could be used for the working electrode, reference electrode, and electrolyte, in the illustrative embodiment the working electrode 13 is platinum while the reference electrode 25 is silver and the electrolyye is silver chloride. The apparatus of the invention is more sensitive than available commercial concentration detectors, being capable of detecting down to parts per billion of chlorine. The sensitivity of the cell is proportional to the surface area of the electrodes and the configuration used permits the electrodes in the present apparatus to have a relatively large surface area. The speed of response of the apparatus is inversely proportional to the spacing between the cell electrodes.

The calibration cell is comprised of working electrode 6 disposed in passageway 3 by threaded plastic mounting means 15 and reference electrode 17 disposed in vertical passageway 16 having an electrolyte therein. A suitable mounting means for the reference electrode is plastic cap 18 which is threaded into passageway 16 and which has a threaded hole through its center through which plastic electrode mounting means 19 is threaded. As in the case of the detecting cell the electrodes and electrolyte of the calibration cell may be made of any suitable materials, and in the illustrative embodiment the working electrode is platinum while the reference electrode is silver and the electrolyte is saturated silver chloride and potassium chloride.

Vertical reference electrode passageways 32 and 16 each have a small horizontal hole disposed in a sidewall of the passageway and leading to passageways 61 and 9, respectively. To enable ionic transportation between the detecting and calibrating cell electrolytes and the remainder of the fluidic system while preventing the electrolytes from escaping from passageways 32 and 16, passageways 61 and 79 connected to electrolyte passageway 32 are filled with silica gel as are passageways 9 and 8 leading from electrolyte passageway 16.

In FIG. 2 the far end of passageway 3 is closed with plug 4 and the near end of passageway 10 is closed with plug 35. Vertical passageway 31 comprises an outlet for the fluid. Passageway portions 26, 27, 62, 28, 29 and 30 are blocked, for instance by being filled with plastic, these portions being present only because the plastic block is drilled from the exterior and so any passageways which are not intended to extend to the exterior of the block must be filled. In FIG. 2, the fluid flow path through the assembly is through passageways 2, 3, 7, 10, 11, 12, and 31. The silica gel prevents the fluid from entering passageways 8 and 79 while enabling ionic interaction between the fluid and the electrodes.

The operation of the apparatus will now be described in conjunction with FIGS. 1 to 4. Referring to FIG. 1, the water sample enters the system upstream of pipe portion 40 and is pumped by pump 41 through pipe portion 63 as well as the remainder of the system. A 0.1M potassium iodide solution in a pH 4 buffer and saturated with NaCl is contained in container 42 and flows at a constant, relatively slow rate through T-section 43 where it is mixed with the water sample. An exemplary ratio of potassium iodide to water which may be used in the apparatus of the invention is 1:1000 but the specific ratio used is not important as long as there is enough potassium iodide to react with all of the chlorine in the water. The purpose of adding NaCl is to increase the electrical conductivity of the water sample, since electrical current must flow in both the detector and the calibrator. In an exemplary embodiment where the goal was to react the potassium iodide with the total residual chlorine in the water rather than to determine individual chlorine species, the pH chosen for the water was 4.

In the chemical reaction between the chlorine in the water and the potassium iodide, one mole of chlorine produces one mole of iodine as follows:

Similar reactions may be written for the hypochlorite ion and the chloramines, but the results of the measurement can be referred to a single reference state as though elemental chlorine were present. Thus, monitoring the molar concentration of iodine is equivalent to monitoring the effective molar concentration of chlorine when the above intermediate reaction is employed.

To monitor the concentration of iodine, the iodine detecting cell means described above and having electrodes 13 and 25 is employed. As described above, the solution comprised of the water mixed with the potassium iodide flows through passageways 2, 3, 7, 10, 11, 12, and out passageway 31.

Since electrically the fluid flows between the electrodes of the detecting cell, the cell generates an amount of current proportional to the concentration of the iodine in the fluid. The detecting cell is connected to electronics package 46 by wires 21 and 22 and the electronics package displays at 68 either the current itself or the current converted to concentration (parts per million or per billion) of chlorine.

To calibrate the apparatus, the calibration cell means described above and having electrodes 6 and 17 is provided. The function of this cell is to coulometrically generate a known and predetermined amount of iodine at a known rate. The iodide in the potassium iodide is oxidized to iodine by the calibration cell at the platinum working electrode as follows:

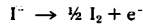

The rate of this oxidation is determined by the electrical current imposed upon the calibration cell. To achieve control of the oxidation, the electronics package is provided with a variable, effective constant current source which is inputted to the calibration cell at leads 20 and 23. According to Faraday's Law, the number of equivalents, n, of substance produced in an electrolysis cell is proportional to the charge, Q, passed through the cell, $$n = Q/F$$

where F is the Faraday's constant. $Q = \int I dt$ where $i$ is the imposed current. The differential form of this equation is thus $$dn/dt = i/F$$

where $i$ = const. so that electrical current flowing through the calibration cell in the monitoring system is proportional to the flux of generated iodine with Faraday's constant as the proportionality constant. Consequently, the electrochemically generated iodine flux needed to produce an amperometric signal identical to the signal obtained from unknown water, corresponds to the unknown chlorine concentration.

The apparatus may be calibrated using a sample of either distilled or undistilled water. The faceplate of a typical electronics package used is shown in FIG. 5 and the specific circuits used can be conventional. If distilled water is used then all of the iodine measured (except for the residual iodine contained by the potassium iodide) is due to the coulometric generation. Referring to FIG. 5 selector switch 50 would be set to "calibrate", thus enabling a constant current generator in the electronics package and the particular current value used would be selected by switch 52. Since the value of iodine displayed on display 68 (which can be a digital display) is known according to Faraday's Law calibrate control 48 is adjusted so that the display reads the correct value. Calibrate control 48 may be a potentiometer which controls the gain of an amplifier inside the package. The apparatus is designed to operate with a specific sample flow rate and if the flow rate is off the meter reading must be corrected either by changing the flow rate or with the gain control. Since potassium iodide contains some residual iodine this must be cancelled as part of the calibration process and this is accomplished by adjusting base line offset control 51, which may for instance control the offset of an operational amplifier. Thus each time the reagent supply is changed the apparatus must be re-calibrated. If the sample water is used for calibration instead of distilled water calibration is effected on the basis that the amount of iodine added to that produced by the chemical reaction is known. The remainder of the controls and inputs shown on the faceplate of FIG. 5 are illustrative, and as they do not form part of the invention, they will not be described in detail.

Figure 6:
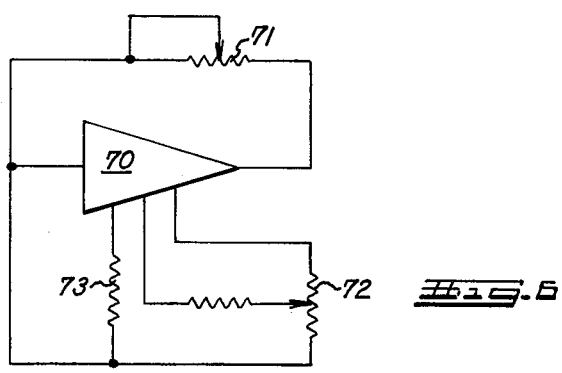
FIG. 6 is a schematic diagram illustrating the electronic principle behind the calibrate (gain) and baseline offset controls shown in FIG. 5.

FIG. 6 is a circuit which illustrates the electronic principle utilized in the calibration. In FIG. 6 operational amplifier 70 has feedback gain control 71 and potentiometric offset control 72, and a circuit such as this (or utilizing this principle) may be tied to controls 48 and 51 in FIG. 5.

Further, while I have described an illustrative embodiment of my invention, I wish it to be understood that I do not intend to be restricted solely thereto, but that I do intend to cover all modifications thereof which would be apparent to one skilled in the art and which come within the spirit and scope of my invention.

What is claimed is:

1. Apparatus for measuring low concentration levels of chlorine in water including a self-contained calibration means comprising, means for providing a sample of water, a container of potassium iodide solution, means for mixing said sample of water and said potassium iodide solution to form a new solution, said new solution containing an amount of iodine proportional to the concentration of the chlorine in said sample of water, amperometric detecting cell means having a reference electrode and a working electrode, means for passing said new solution between said electrodes of said detecting cell means, and means for measuring the electrical current output of said detecting cell means, said calibration means comprising electrolysis cell means situated upstream of said detecting cell means for electrolyzing the potassium iodide in said new solution to iodine when operated, and means for passing said new solution through said electrolysis cell means before it is passed through said detecting cell means.

2. The apparatus of claim 1 wherein said calibration means further includes a means for turning said electrolysis cell means on and off, and a means for controlling the amperage of the current fed through said electrolysis cell means when on, said cell being left off except when calibrating and said amperage being proportional to the amount of iodine generated.

3. The apparatus of claim 2 wherein said means for passing said new solution between said electrodes of said detecting cell means comprises at least a passageway in a solid plastic block, said working electrode of said detecting cell means comprising an elongated coiled wire disposed in a passageway of said at least a passageway, said plastic block having a plurality of interconnected passageways and said new solution being fed to said block via an entrance passageway and leaving said block via an exit passageway.

4. The apparatus of claim 3 wherein said electrolysis cell means has a reference electrode and a working electrode and said working electrode comprises an elongated coiled wire disposed in one of said plurality of interconnected passageways upstream of said detecting cell means.

5. The apparatus of claim 4 wherein said reference electrodes of both said cell means are situated in passageways in said plastic block which are disposed perpendicularly to said passageways in which said working electrodes are disposed.

6. The apparatus of claim 5 wherein an electrolyte is disposed in said reference electrode passageways, at least one of said interconnected passageways connecting with each of said reference electrode passageways and being perpendicular thereto being filled with silica gel to facilitate ionic transport to said electrolyte but to prevent said electrolyte from escaping from said reference electrode passageways.

* * * * *